US00PP25687P2

(12) United States Plant Patent
Heus

(10) Patent No.: US PP25,687 P2
(45) Date of Patent: Jul. 7, 2015

(54) ***LOBELIA* PLANT NAMED 'BLACK TRUFFLE'**

(50) Latin Name: *Lobelia cardinalis*
Varietal Denomination: Black Truffle

(71) Applicant: Peter Heus, Hinton, WV (US)

(72) Inventor: Peter Heus, Hinton, WV (US)

(73) Assignee: Plants Nouveau, LLC, Charleston, SC (US)

( * ) Notice: Subject to any disclaimer, the term of this patent is extended or adjusted under 35 U.S.C. 154(b) by 79 days.

(21) Appl. No.: 13/998,505

(22) Filed: Nov. 6, 2013

(51) Int. Cl.
*A01H 5/02* (2006.01)

(52) U.S. Cl.
USPC ..... Plt./451

(58) Field of Classification Search
USPC ..... Plt./451
CPC ..... A01H 5/02; A01H 5/00
See application file for complete search history.

*Primary Examiner* — Kent L Bell
(74) *Attorney, Agent, or Firm* — Penny J. Aguirre

(57) ABSTRACT

A new cultivar of hybrid *Lobelia*, 'Black Truffle', that is characterized by its deep purple-black foliage, its deep red flowers, and its dependable perennial plant habit.

2 Drawing Sheets

Botanical classification: *Lobelia cardinalis*.
Variety denomination: 'Black Truffle'.

BACKGROUND OF THE INVENTION

The present invention relates to a new and distinct cultivar of *Lobelia cardinalis* and will be referred to hereafter by its cultivar name, 'Black Truffle'. 'Black Truffle' is an herbaceous perennial grown for landscape use.

The Inventor selected 'Black Truffle' in May of 2010 in a trial bed in Landenberg, Pa. The Inventor planted seeds of unnamed plants of *Lobelia cardinalis* and selecting and reselecting open pollinated plants over a period of ten years prior to selecting 'Black Truffle' as a single unique plant.

Asexual propagation of the new cultivar was first accomplished by the Inventor by vegetative stem cuttings in June 2011 in Landenberg, Pa. Asexual propagation by vegetative stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Black Truffle' as a unique cultivar of *Lobelia*.

1. 'Black Truffle' exhibits deep purple-black foliage.
2. 'Black Truffle' exhibits deep red flowers.
3. 'Black Truffle' exhibits a dependable perennial plant habit.

Typical plants of the parent species differ from 'Black Truffle' in having green foliage and in having flowers that are lighter red in color. 'Black Truffle' can also be most closely compared the *Lobelia cardinalis* cultivars 'Green Fried Tomatoes' (U.S. Plant Pat. No. 21,958) and 'Golden Torch' (U.S. Plant Pat. No. 19,844). 'Green Fried Tomatoes' differs from 'Black Truffle' in having foliage that is green with a purple overlay (not as dark purple in color) and in having flowers that are lighter red in color. 'Golden Torch' differs from 'Black Truffle' in having yellow-green foliage, a less robust plant habit, a smaller plant size, and flowers that are lighter red in color.

BRIEF DESCRIPTION OF THE DRAWING

The accompanying colored photographs illustrate the overall appearance and distinct characteristics of the new *Lobelia* as grown in a garden in Hinton, W. Va.

The photograph in FIG. 1 was taken of a plant two-years in age and provides a view of 'Black Truffle' in bloom.

Figure 1:
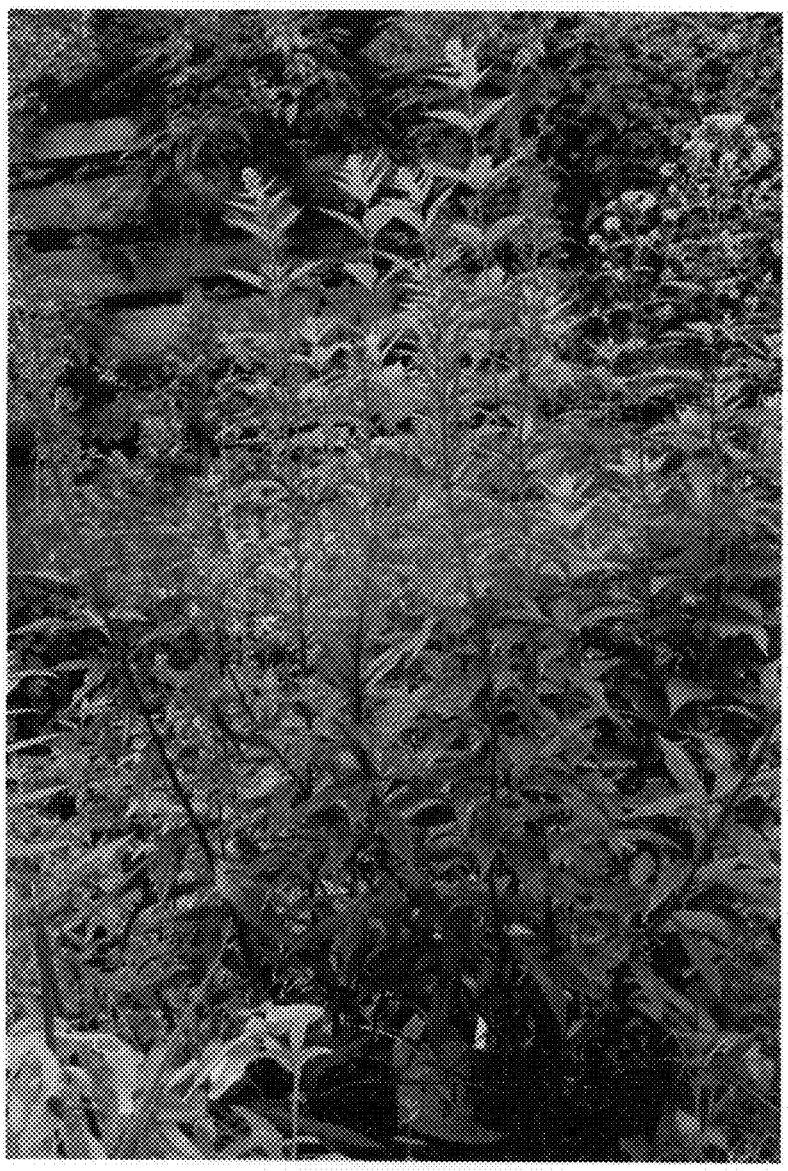
Figure 2:
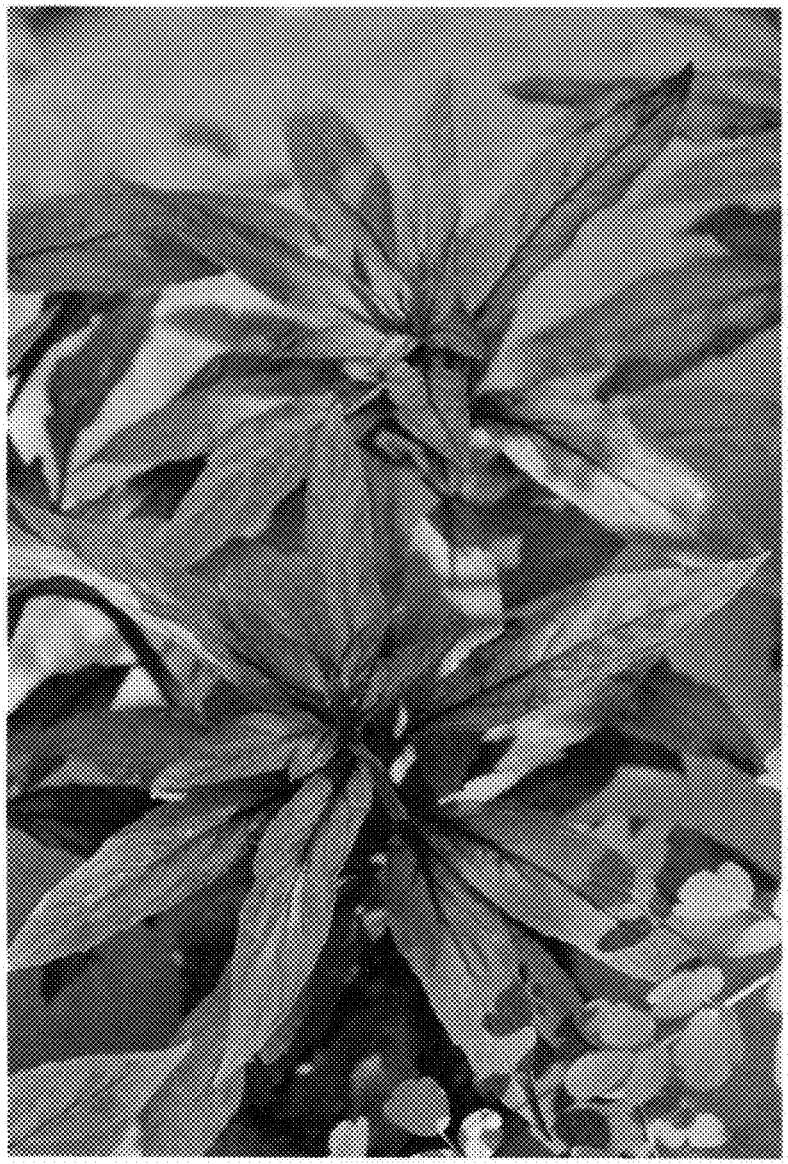

The photograph in FIG. 2 was taken of a plant one year in age and provides a close-up view of the foliage of 'Black Truffle'.

The colors in the photographs may differ slightly from the color values cited in the detailed botanical description, which accurately describe the colors of the new *Lobelia*.

DETAILED BOTANICAL DESCRIPTION

The following is a detailed description of the new cultivar of plants 2 years in age as grown outdoors in a garden in Boston, Mass. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—From July through September in Massachusetts.

*Plant type*.—Herbaceous perennial with a dependable perennial habit.

*Plant habit*.—Upright, bushy.

*Plant size*.—Reaches about 1 m in height and 45 cm in spread without pinching.

*Hardiness*.—At least to U.S.D.A. Zones 3 to 9.

*Diseases and pests*.—No susceptibility or resistance to diseases or pests has been observed.

*Root description*.—Fibrous, non-spreading.

*Propagation*.—Vegetative stem cuttings.

*Growth rate*.—Moderate.

Stem description (flower scape):

*Stem color*.—New growth; N79A, mature stems; N77A.

*Stem size*.—Stem base; about 1 cm in diameter, main stems; an average of 5 mm in diameter and 110 cm in length (including the inflorescence), lateral branches; average of 3 mm in diameter and up to 30 cm in length.

*Stem surface*.—New growth; pubescent, mature stems; sparsely covered with glandular hairs, base of stem; fissured (bark-like).

*Internode length*.—Average of 12 cm between branches and 4 cm between leaves.

*Branching*.—Average of 8 main stems and an average of 5 lateral braches per main stem.

Foliage description:

*Basal foliage*.—Leaf shape. — Oblanceolate. Leaf division. — Simple. Leaf base. — Cuneate. Leaf apex. — Acute to acuminate. Leaf fragrance. — None. Leaf venation. — Pinnate, 187B in color on the upper and lower surfaces. Leaf margins. — Serrated. Leaf arrangement. — Rosulate. Leaf attachment. — Petiolate. Leaf surface. — Glabrous and lustrous on upper surface and lower surface. Leaf size. — Up to 10 cm in length and 4 cm in width. Leaf color. — Newly expanded leaves; upper surface N77A, lower surface a blend of N77A and 187A to 187B, mature leaves; upper surface a blend of 147A and 187C, lower surface 187A to 187C. Petioles. — Up to 2.5 cm in length and 3 mm in width, upper surface a blend of 187C and 147B with 147A at the margins and lower surface a blend of 187B and 195B in color, glabrous and lustrous surface.

*Cauline foliage*.—Leaf shape. — Oblanceolate. Leaf division. — Simple. Leaf base. — Cuneate. Leaf apex. — Acute to acuminate. Leaf fragrance. — None. Leaf venation. — Pinnate, N77C in color on the upper surfaces and N186C on lower surfaces. Leaf margins. — Serrated. Leaf arrangement. — Rosulate. Leaf attachment. — Petiolate. Leaf surface. — Glabrous and lustrous on upper surface and lower surface. Leaf size. — Up to 17 cm in length and 4 cm in width. Leaf color. — Newly expanded leaves; upper surface N200A with highlights of N189B, lower surface N77A, mature leaves; upper surface N187A, lower surface 185C. Petioles. — Up to 1.5 cm in length and 3 mm in width, upper surface color 186B, lower surface color N144C, glabrous and lustrous surface.

Inflorescence description:

*Inflorescence type*.—Terminal branched raceme of bilabiate flowers.

*Lastingness of inflorescence*.—Individual flowers about 3 days.

*Inflorescence size*.—An average of 60 cm in length and 5 cm in width.

*Flower type*.—Tubular-bilabiate.

*Flower number*.—An average of 101 per inflorescence.

*Flower fragrance*.—None.

*Flower buds*.—Tubular in shape, about 1.5 cm in length and 0.5 mm in diameter, color: 46B (calyx portion), apex is 46B.

*Flower size*.—Up to 3.5 cm in length (including extended pistil) and 0.5 cm in diameter.

*Peduncle* (*rachis*).—An average of 2 cm in length and 1 mm in width, 187A in color, surface is densely covered with glandular hairs, flower internode length an average of 2 cm.

*Pedicels*.—About 1.5 mm in length and 1 mm in width, 194A in color, surface is pubescent.

*Calyx*.—Tubular, up to 2 cm in length and 1 cm in width, persistent for about a week after petals drop.

*Sepals*.—5, fused at base with every apex free that is triangular in shape, 15 mm in length and 3 mm in width, apex mucronate, entire margin, 197A in color, surface is finely puberulent and lustrous.

*Petals*.—5, arranged in 2 lips fused into tube at base, tube; about 1.5 cm in length and 0.5 in width, 45A in color, lustrous surface, upper lip; 4-lobed, held upright to tube and slightly protruding outward, curved into renal shape around pistil and stamens, about 1.5 cm in length and 2 mm in width, 45A in color, velvety on outer surface and lustrous on inner surface, apex single notched, base fused to tube, lower lip; 2 fused lobes, oval in shape with sides recurved, margin entire, apex 2 notched, base fused, surface velvety on upper surface and lustrous on lower surface, about 1.5 cm in length and 2 mm in width, 42B in color.

Reproductive organs:

*Gynoecium*.—1 pistil, about 3 cm in length with about 1 cm exserted beyond corolla, style is about 2.5 cm in length, 1 mm in width and 164A in color, stigma is bifid with arms about 5 mm in length, linear in shape and N187A in color, ovary is superior, oblong in shape, about 5 mm in length and 5 mm in diameter and 141D in color.

*Androcoecium*.—5 stamens, filaments are 196C in color, about 2 cm in length and 1 mm in width, attached to lobe sides with linear arms about 4 mm in length and 174B in color and fused at base, anthers are an average of 1 mm in length, 199C in color and dorsifixed, pollen is abundant in quantity and about 196C in color.

*Fruit and seed*.—Observed to be sterile with no viable seeds formed.

It is claimed:

1. A new and distinct cultivar of *Lobelia* plant named 'Black Truffle' as herein illustrated and described.

* * * * *